(12) United States Patent
Mohanty et al.

(10) Patent No.: US 8,545,819 B2
(45) Date of Patent: Oct. 1, 2013

(54) ORAL CARE TOOTHPOWDER COMPOSITION WITH FLUORIDE ION SOURCE

(75) Inventors: Arjya Bhushan Mohanty, Drissa (IN); Ripen Misri, Maharashtra (IN)

(73) Assignee: Colgate-Palmolive Company, New York, NY (US)

( * ) Notice: Subject to any disclaimer, the term of this patent is extended or adjusted under 35 U.S.C. 154(b) by 644 days.

(21) Appl. No.: 11/413,623

(22) Filed: Apr. 28, 2006

(65) Prior Publication Data

US 2007/0025929 A1     Feb. 1, 2007

Related U.S. Application Data

(63) Continuation of application No. 11/218,954, filed on Sep. 2, 2005, now abandoned, which is a continuation of application No. 11/020,013, filed on Dec. 21, 2004, now abandoned.

(51) Int. Cl.
*A61K 8/00*     (2006.01)
*A61K 8/21*     (2006.01)

(52) U.S. Cl.
USPC ............................................ 424/49; 424/52

(58) Field of Classification Search
None
See application file for complete search history.

(56) References Cited

U.S. PATENT DOCUMENTS

| | | | |
|---|---|---|---|
| 2,196,150 A * | 4/1940 | Heald et al. .................... 424/57 |
| 4,423,030 A | 12/1983 | Hayes et al. |
| 4,512,741 A | 4/1985 | Mushta |
| 4,547,362 A * | 10/1985 | Winston et al. ................. 424/49 |
| 4,861,590 A * | 8/1989 | Grodberg ...................... 424/602 |
| 4,960,597 A | 10/1990 | Farbood et al. |
| 5,156,845 A * | 10/1992 | Grodberg ...................... 424/440 |
| 5,182,101 A | 1/1993 | Wuelknitz et al. |
| 5,248,228 A * | 9/1993 | Giardina ........................ 406/56 |
| 5,320,862 A | 6/1994 | La Tona |
| 6,294,161 B1 | 9/2001 | Hiramoto et al. |
| 6,322,838 B1 | 11/2001 | Güntert et al. |
| 6,375,933 B1 | 4/2002 | Subramanyam et al. |
| 6,379,652 B1 | 4/2002 | Liu et al. |
| 6,518,227 B2 | 2/2003 | Woosley |
| 6,680,289 B1 | 1/2004 | Woo et al. |
| 6,689,342 B1 | 2/2004 | Pan et al. |
| 6,733,798 B2 | 5/2004 | Heeg et al. |
| 6,740,311 B2 * | 5/2004 | White et al. .................... 424/49 |
| 2003/0206874 A1 | 11/2003 | Doyle et al. |
| 2004/0091429 A1 * | 5/2004 | Flemmig et al. ............... 424/49 |

* cited by examiner

*Primary Examiner* — Brian Gulledge
*Assistant Examiner* — Snigdha Maewall
(74) *Attorney, Agent, or Firm* — Howard C. Lee

(57) ABSTRACT

A toothpowder oral care composition of fluoride ion source particulate (such as stannous fluoride particulate) dispersed in an oral calcium carbonate abrasive particulate bed is achieved with careful adjustment of the particle sizes of both the fluorinated particulate and the abrasive particulate to achieve a bed of toothpowder where neither the fluorinated particulate or the abrasive particulate will settle to create a localized concentration of the fluoride significantly different from the average concentration of the fluoride throughout the bed.

15 Claims, No Drawings

ORAL CARE TOOTHPOWDER COMPOSITION WITH FLUORIDE ION SOURCE

CROSS-REFERENCE TO RELATED APPLICATIONS

This application is a continuation of U.S. patent application Ser. No. 11/218,954, filed Sep. 2, 2005, now abandoned, which is a continuation of U.S. patent application Ser. No. 11/020,013 filed Dec. 21, 2004, now abandonded, the contents of each of which are incorporated herein by reference.

BACKGROUND OF THE INVENTION

Oral care compositions are used for a wide variety of purposes, including for enhancing personal health, hygiene, and appearance, as well as for preventing or treating a variety of diseases and other conditions in humans and in animals.

The formulation of such compositions presents a number of challenges. They must be pharmaceutically and/or cosmetically acceptable for their intended use. Compositions that contain therapeutic active materials preferably deliver the active at effective levels, avoiding undue chemical degradation. Similarly, compositions containing cosmetically functional materials must deliver the material to the oral cavity at effective levels under the conditions that they are typically used by the consumer.

Moreover, the aesthetic appeal of all such compositions is important, and can have significant effects on consumer acceptance and usage. Aesthetic effects have been acknowledged to play an important role in consumer acceptance of many products. Although such products have met with consumer approval, the art seeks to further improve the aesthetic effects as well as the cosmetic and therapeutic benefits of these products. Indeed, many such compositions known in the art are deficient in one or more attributes. Thus, there is an ongoing need for new oral care compositions, and methods of their use.

Fluoride is a very well known anti-cavity agent, widely used in toothpaste. However, fluoride use in toothpowder is complicated because of settling issues. In this regard, fluoride needs to be controlled to provide, for instance, a maximum of 1000 parts per million of soluble fluoride ion in some countries and a maximum of 1500 parts per million of soluble fluoride ion in other countries; and settling of a toothpowder fluoride ion source within a toothpowder container is of concern insofar as localized fluoride ion concentrations might be elevated above the acceptable level by such settling. Toothpaste is usually formulated to have a viscosity that preempts such settling in fluoride ion sources within the toothpaste, but toothpowder needs to provide a movable particulate so that the powder can be poured for use.

However, the effectiveness of toothpowder in providing a fluoride ion source is therefore adversely affected because of this challenge respective to the composition and consumer compliance.

SUMMARY

The present invention provides oral care compositions. In somewhat greater detail, the invention is for toothpowder of clinically efficacious fluoride ion source particulate dispersed in an orally acceptable abrasive calcium carbonate particulate bed.

In another aspect, the fluoride ion source particulate is any of particulate sodium monofluorophosphate, particulate sodium fluoride, particulate stannous fluoride, or combinations thereof.

In a further aspect where the fluoride ion source is particulate sodium monofluorophosphate, particulate sodium fluoride, particulate stannous fluoride or combinations thereof, the bed has a volume of at least 125 cubic millimeters, at least 99 percent of individual calcium carbonate particles in the bed have an independent calcium carbonate particle size from about 10 to about 150 microns, at least 99 percent of individual fluoride ion source particulate particles in the set have an independent fluoride ion source particulate particle size from about 10 to about 150 microns, and any 125 cubic millimeter volumetric portion of the bed has a concentration of fluoride ion source providing from about 500 to about 1500 parts per million of soluble fluoride respective to calcium carbonate.

In further aspects dispersed sodium lauryl sulfate particulate, dispersed saccharin particulate, citric acid, and/or flavor oil are added into the toothpowder as described above.

In yet a further aspect where the fluoride ion source particulate comprises sodium monofluorophosphate, a particulate bed of the toothpowder has a volume of at least 125 cubic millimeters and comprises from about 60 to about 98 weight percent calcium carbonate, from about 0.38 to about 1.14 weight percent sodium monofluorophosphate, from about 0.5 to about 3.5 weight percent sodium lauryl sulfate, from about 0.02 to about 0.5 weight percent saccharin, from about 0.05 to about 0.4 weight percent citric acid, and from about 0.5 to about 3.5 weight percent flavor oil.

The invention is also for admixing clinically efficacious fluoride ion source particulate into orally acceptable abrasive particulate according to any of the above-described formulations.

In yet a further aspect the admixing is performed by use of a ribbon blender.

In yet a further aspect the ribbon blender has a first end and a second end and the admixing is performed by charging the blender with the calcium carbonate and continuously adding a first pulverized stream of particulated fluoride ion source material to the first end of the ribbon blender and a second pulverized stream of particulated fluoride ion source material to the second end of the ribbon blender until the particulated fluoride ion source material is admixed into the calcium carbonate particulate.

In another aspect, the invention provides a method for cleaning teeth by brushing the teeth with about 1 gram of the toothpowder according to the above-described formulation.

It has been discovered that compositions and methods of this invention afford advantages over oral care compositions among known in the art.

Further areas of applicability will become apparent from the detailed description provided hereinafter. It should be understood that the detailed description and specific examples, while indicating embodiments of the invention, are intended for purposes of illustration only and are not intended to limit the scope of the invention.

DESCRIPTION

The following definitions and non-limiting guidelines must be considered in reviewing the description of this invention set forth herein. The headings (such as "Introduction" and "Summary,") and sub-headings (such as "Compositions" and "Methods") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof. Classification or discussion of a material within a section of this specification as having a particular utility (e.g., as being an "active" or a "carrier" ingredient) is made for convenience, and no inference should be drawn that the material must necessarily or solely function in accordance with its classification herein when it is used in any given composition.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features. Specific Examples are provided for illustrative purposes of how to make and use the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in the materials, compositions, devices, and methods of this invention.

As used herein, the term "about," when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

As referred to herein, all compositional percentages are by weight of the total composition, unless otherwise specified.

Compositions

The present invention provides toothpowder as oral care compositions and methods for administration or application to, or use with, a human or other animal subject. In overview, a toothpowder oral care composition of fluoride ion source particulate (such as stannous fluoride, sodium fluoride, and/or sodium monofluorophosphate particulate) dispersed in an oral abrasive calcium carbonate particulate bed is achieved with careful adjustment of the particle sizes of both the fluorinated particulate and the abrasive particulate to achieve a bed of toothpowder where neither the fluorinated particulate or the abrasive particulate will settle to create a localized concentration of the fluoride significantly different from the average concentration of the fluoride throughout the bed of toothpowder.

As referred to herein, an "oral care composition" is any composition that is suitable for administration or application to the oral cavity a human or animal subject for enhancing the health, hygiene or appearance of the subject, preferably providing such benefits as: the prevention or treatment of a condition or disorder of the teeth, gums, mucosa or other hard or soft tissue of the oral cavity; the prevention or treatment of a systemic condition or disorder; the provision of sensory, decorative or cosmetic benefits; and combinations thereof. In various preferred embodiments, an oral care composition is not intentionally swallowed, but is rather retained in the oral cavity for a time sufficient to effect the intended utility. Preferably, specific materials and compositions to be used in this invention are, accordingly, pharmaceutically- or cosmetically-acceptable, clinically effective, and/or clinically efficacious. As used herein, such a "pharmaceutically acceptable" or "cosmetically acceptable", "clinically effective", and/or "clinically efficacious" component is one that is suitable for use with humans and/or animals and is provided in an appropriate amount (a clinically efficacious amount) to provide the desired therapeutic, prophylactic, sensory, decorative, or cosmetic benefit without undue adverse side effects (such as toxicity, irritation, and allergic response) commensurate with a reasonable benefit/risk ratio.

Orally Acceptable Carrier

The present invention provides toothpowder compositions comprising an orally acceptable carrier. Such a carrier comprises a material or combination of materials that is safe for use in the compositions of the present invention, commensurate with a reasonable benefit/risk ratio, with which flavor oil and natural calcium carbonate may be intrinsically associated while retaining significant efficacy. In use, the carrier provides an orally acceptable particulate bed. As used herein, an "orally acceptable particulate bed" refers to a quantity of the composition for application to the teeth of a human or other animal subject in a single use. In various embodiments, the bed has a minimum weight of about 1 gram, conforming to a volume of about 0.95 cc., for application to the teeth in a single instance of a tooth brushing operation. In packaged form for consumer purchase, the bed varies from a size of about 10 grams in a sachet up to about 300 grams in a large can. In manufacturing operations, the bed constitutes a normal charge for a mixing system such as a ribbon blender.

Materials among those that are useful in carriers include adhesion agents, surfactants, foam modulators, abrasives, pH modifying agents, humectants, mouth feel agents, sweeteners, flavorants, colorants, and combinations thereof. It is understood that while general attributes of each of the above categories of materials may differ, there may be some common attributes and any given material may serve multiple purposes within two or more of such categories of materials. Preferably, such carrier materials are selected for compatibility with fluoride ion source and with other ingredients of the composition.

Mouth-feel agents include materials imparting a desirable texture or other feeling during use of the composition. Such agents include dispersed flavorants and sweeteners.

Flavorants among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof. One or more flavorants are optionally present in a total amount of about 0.01% to about 5%, optionally in various embodiments from about 0.05 to about 2%, from about 0.1% to about 2.5%, and from about 0.1 to about 0.5%.

Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof. One or more sweeteners are optionally present in a total amount depending strongly on the particular sweetener(s) selected, but typically at levels of from about 0.005% to about 5%, optionally from about 0.01% to about 1%.

Colorants among those useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of about 0.001% to about 20%, for example about 0.01% to about 10% or about 0.1% to about 5%.

Active Materials

The compositions of the present invention optionally comprise a fluoride ion providing material as an active material, which is operable for the prevention or treatment of a condition or disorder of hard or soft tissue of the oral cavity, the prevention or treatment of a physiological disorder or condition, or to provide a cosmetic benefit. In various embodiments, the active is a "systemic active" which is operable to treat or prevent a disorder which, in whole or in part, is not a disorder of the oral cavity. In various embodiments, the active is an "oral care active" operable to treat or prevent a disorder or provide a cosmetic benefit within the oral cavity (e.g., to the teeth, gingiva or other hard or soft tissue of the oral cavity). Oral care actives among those useful herein include whitening agents, anticaries agents, tartar control agents, antiplaque agents, periodontal actives, abrasives, breath freshening agents, malodour control agents, tooth desensitizers, salivary stimulants, and combinations thereof. It is understood that while general attributes of each of the above categories of actives may differ, there may some common attributes and any given material may serve multiple purposes within two or more of such categories of actives.

Actives useful herein are present in the compositions of the present invention in safe and effective amounts. A "safe and effective" and "clinically efficacious" amount of an active is an amount that is sufficient to have the desired therapeutic or prophylactic effect in the human or lower animal subject to whom the active is administered, without undue adverse side effects (such as toxicity, irritation, or allergic response), commensurate with a reasonable benefit/risk ratio when used in the manner of this invention. The specific safe and effective ("clinically efficacious") amount of the active will vary with such factors as the particular condition being treated, the physical condition of the subject, the nature of concurrent therapy (if any), the specific active used, the specific dosage form, the carrier employed, and the desired dosage regimen.

The compositions of the present invention further comprise an abrasive in the preferred form of calcium carbonate particulate. In various embodiments, an additional optional abrasive is useful for example as a polishing agent. Any orally acceptable abrasive can be used, but type, fineness (particle size) and amount of abrasive should be selected so that tooth enamel is not excessively abraded in normal use of the composition. Suitable optional abrasives include silica, for example in the form of precipitated silica or as admixed with alumina, insoluble phosphates, calcium carbonate, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

The compositions of the present invention optionally comprise a tartar control (anticalculus) agent. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane- 1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof.

The compositions of the present invention comprise a fluoride ion source useful, for example, as an anti-caries agent. Any orally acceptable particulated fluoride ion source can be used, including potassium, sodium and ammonium fluorides and monofluorophosphates, stannous fluoride, indium fluoride, amine fluorides, including olaflur (N'-octadecyltrimethylendiamine-N,N,N'-tris(2-ethanol)-dihydrofluoride), and mixtures thereof. Particulate sodium monofluorophosphate, particulate sodium fluoride, particulate stannous fluoride, and combinations thereof are preferred. One or more fluoride ion sources are optionally present in an amount providing a clinically efficacious amount of soluble fluoride ion from about 500 to about 1500 ppm in any bed quantity of not less than about 1 gram.

The compositions of the present invention optionally comprise a saliva stimulating agent, useful for example in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in a saliva stimulating effective total amount.

The compositions of the present invention optionally comprise a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), and mixtures thereof.

Methods of Manufacture

The toothpowder compositions of the present invention are made by methods; these methods including pulverizing (and, optionally, screen filtering) of oral care active particles so that all particles of oral care active are comparably sized to particles of their orally acceptable carrier bed such that a bed of admixed oral care active particulate and orally acceptable calcium carbonate particulate will not significantly differentiate the oral care active compositionally between any first 1 gram portion of the bed and any other 1 gram portion of the same bed. The methods also include mixing of the oral care active particulate and orally acceptable calcium carbonate particulate in a system such as a ribbon blender. In one embodiment, the oral care active particulate and orally acceptable calcium carbonate particulate are pulverized so that, in a bed having a volume of at least 125 cubic millimeters, at least 99 percent of individual calcium carbonate particles in the bed have an independent calcium carbonate particle size from about 10 to about 150 microns (preferably from about 13 to about 34 microns), at least 99 percent of individual fluoride ion source particulate particles in the set have an independent fluoride ion source particulate particle size from about 10 to about 150 microns (preferably from about 13 to about 34 microns), and any 125 cubic millimeter volumetric portion of the bed has a concentration of fluoride ion source providing from about 500 to about 1500 parts per million of soluble fluoride respective to calcium carbonate.

To achieve appropriate dispersion and utility, the particulates are also pulverized to a size that essentially precludes agglomeration between particulates in the bed that could confound comprehensive dispersion and mixing of the fluoride ion source particles into the orally acceptable carrier bed. In one embodiment, the bed is dried or otherwise treated to minimize surface tension between particles that could lead to such agglomeration.

In one embodiment, a uniform dispersion of fluoride in the tooth powder and major abrasive is achieved, after adjusting of the particle size distribution of the oral care active particulate (fluoride ion source) to match the major abrasive (calcium carbonate particulate) particle size is first performed, by adding the fluoride ion source particulate into both ends of a ribbon blender mixer. In this regard, ribbon blenders have a U-shaped horizontal trough (with the U shape of the inner shell being apparent when viewed from the end cross section of the trough in parallel view along the trough axis) and a specially fabricated elongated ribbon agitator positioned to rotate about the trough axis in the generally semi-circular portion of the trough conformant to the lower part of the U. The ribbon agitator has at least one inner helical agitator and at least one outer helical agitator. In operation at least one helical agitator (ribbon) thereby rotates to "drive" material in the leftward (as viewed in trough axial cross section perpendicular to the trough axis) direction of the trough and at least one helical agitator (ribbon) rotates to "drive" material in the (opposite) rightward direction.

The trough (ribbon blender) has two ends (each conforming to the U shape in parallel view along the trough axis). In one embodiment, the abrasive particulate is charged to the ribbon blender, the charged abrasive particulate is then agitated, and the blending of fluoride ion source particulate and major abrasive particulate (calcium carbonate particulate) to fully disperse the oral care active particulate (fluoride ion source) is achieved by continuous addition of the fluoride ion source particulate over a period of time to both of the two ends of the ribbon blender during agitation of the calcium carbonate abrasive particulate. In this regard, addition at both ends appears to minimize challenges in localized concentration of the fluoride ion source particulate within the toothpowder.

Additional ingredients such as flavorant, coloring, and/or sweeteners are added at any point during the mixing process, but, in various embodiments, such ingredients are preferably added last or close to last.

Methods of Use

The present invention provides methods for cleaning a tooth surface using compositions according to the present invention. As referred to herein, "tooth" or "teeth" refers to natural teeth, dentures, dental plates, fillings, caps, crowns, bridges, dental implants, and the like, and any other hard surfaced dental prosthesis either permanently or temporarily fixed within the oral cavity.

Accordingly, the present invention provides methods for cleaning a tooth surface, comprising applying to the surface a safe and effective amount of about 1 gram of aqueously moistened toothpowder and then agitating the aqueously moistened toothpowder against each surface of the tooth with a toothbrush. As referred to herein, "applying" refers to any method by which the toothpowder is placed in contact with the tooth surface.

In various embodiments, compositions of the present invention are also used for the treatment or prevention of disorders in the oral cavity, including cavity prevention, whitening, plaque prevention or reduction, gingivitis prevention or reduction, tartar control, sensitivity prevention or reduction, breath malodor prevention or reduction, and stain prevention. Compositions of the present invention may also be used for the treatment or prevention of systemic disorders, such as the improvement of overall systemic health characterized by a reduction in risk of development of systemic diseases, such as cardiovascular disease, stroke, diabetes, severe respiratory infection, premature and low birth weight infants (including associated post-partum dysfunction in neurologic/developmental function), and associated increased risk of mortality. Such methods include those disclosed in U.S. Patent Publication 2003/0206874, Doyle et al., published Nov. 6, 2003.

The present invention is further illustrated through the following non-limiting examples.

EXAMPLE 1

A blend of PCC/NCC (precipitated calcium carbonate and natural calcium carbonate) particulate is admixed with a fluoride-ion source of sodium monofluorophosphate (SMFP). Particle size of the PCC/NCC is screened so that 99 percent of the calcium carbonate particles have a particle size from about 10 to about 150 microns. The particle size distribution of SMFP is adjusted to match the PCC/NCC major abrasive so that 99 percent of the SMFP particles have a particle size from about 10 to about 150 microns. The PCC/NCC abrasive particulate is charged to the ribbon blender, and then agitated. Addition of SMFP particulate is done in a controlled manner at the two ends of the ribbon mixer at the rate of approximately 30 gms/minute at the two ends of the ribbon blender. The entire addition time requires 25-30 minutes. Further interblending with additional PCC/NCC abrasive particulate (via addition at both ends) is done and kept under mixing for 50 minutes to provide a tooth powder containing not more than 1000 ppm active fluoride. Samples are taken from different locations of the blender at regular intervals during the mixing operation to validate the uniform dispersion of SMFP in the toothpowder. Sodium lauryl sulfate, saccharin, and flavor are then intermixed to provide a final toothpowder product.

EXAMPLE 2

An intra-oral remineralization-demineralization study is conducted to compare the ability of three toothpowders to promote the hardening of caries-like lesions in enamel. The products evaluated in this study are Toothpowder 1 formulated as essentially described in Example 1, a first commercially-available non-fluorinated toothpowder identified as Toothpowder 2, and a second commercially-available non-fluorinated toothpowder identified as Toothpowder 3. The study design is a double-blind, cross-over with random product assignment. Each product is used twice a day for two weeks. The efficacy of each product is determined by measuring its ability to promote the hardening of partially demineralized blocks of enamel implanted in partial lower mandibular dentures during the two week treatment period. Enamel hardness is measured using a Knoop micro hardness tester. Results are reported as percent changes in hardness before and after treatment. Twenty nine panelists participate in the study.

The results of the study are shown in Table 1.

TABLE 1

Average Percent Change in Enamel Hardness after Treatment of with Three Toothpowders.

| Treatment | N | Average % Hardness Increase ± SD | Statistical Group* |
|---|---|---|---|
| Toothpowder 1 | 29 | +34.4 ± 32.6 | A |
| Toothpowder 2 | 29 | +15.0 ± 47.5 | B |
| Toothpowder 3 | 29 | +11.0 ± 40.0 | B |

A different letter (A or B) indicates a different statistical group in the above table. All three toothpowders promote a net increase in hardness of enamel. A statistical analysis consisting of a two factor ANOVA with the treatment and subject as factors followed by a Tukey multiple T-test is conducted. The results of the analysis show that Toothpowder 1 with fluoride is significantly better than Toothpowder 2 (p=0.03) and Toothpowder 3 (p=0.01) at promoting the hardening of partially demineralized enamel. No significant difference is observed between Toothpowder 2 and Toothpowder 3 (p=0.9). The results of this study show that Toothpowder 1 with fluoride performs significantly better at hardening enamel with caries-like lesions than Toothpowder 2 and Toothpowder 3.

EXAMPLE 3

An evaluation of robustness in dispersion of fluoride is tested by preparing samples of toothpowder having fully dispersed fluoride according to the procedure of Example 1, packaging the toothpowder samples in cans that are appropriately sized for consumer consumption, shipping the canned samples for a distance of more than 2000 Km, and evaluating the samples for dispersion of the fluoride in the toothpowder after the shipping operation. The evaluations indicate that the dispersion of the fluoride remains uniform in the shipped samples.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

What is claimed is:

1. A toothpowder composition comprising a clinically efficacious fluoride ion source particulate selected from sodium monofluorophosphate sodium fluoride, stannous fluoride, and combinations thereof, and an orally acceptable calcium carbonate abrasive particulate wherein in a bed of the toothpowder of a volume of at least 125 cubic millimeters at least 99 percent of individual calcium carbonate particles in said bed have an independent calcium carbonate particle size from about 10 to about 150 microns, at least 99 percent of individual fluoride ion source particulate particles in said set have an independent fluoride ion source particulate particle size from about 10 to about 150 microns, and any 125 cubic millimeter volumetric portion of said bed has a concentration of fluoride ion source providing from about 500 to about 1500 parts per million of soluble fluoride respective to calcium carbonate.

2. The toothpowder of claim 1 further comprising dispersed sodium lauryl sulfate particulate.

3. The toothpowder of claim 1 further comprising dispersed saccharin particulate.

4. The toothpowder of claim 1 further comprising citric acid.

5. The toothpowder of claim 1 further comprising flavor oil.

6. A method for cleaning teeth comprising brushing said teeth with about 1 gram of said toothpowder according to claim 1.

7. A method for making toothpowder, comprising: admixing clinically efficacious fluoride ion source particulate selected from sodium monofluorophosphate, sodium fluoride, stannous fluoride, and combinations thereof, into an orally acceptable calcium carbonate abrasive particulate, wherein in a bed having a volume of at least 125 cubic millimeters, at least 99 percent of individual calcium carbonate particles in said bed have an independent calcium carbonate particle size from about 10 to about 150 microns, at least 99 percent of individual fluoride ion source particulate particles in said set have an independent fluoride ion source particulate particle size from about 10 to about 150 microns, and any 125 cubic millimeter volumetric portion of said bed has a concentration of fluoride ion source providing from about 500 to about 1500 parts per million of soluble fluoride respective to calcium carbonate.

8. The method of claim 7 wherein said admixing admixes dispersed sodium lauryl sulfate into said toothpowder.

9. The method of claim 7 wherein said admixing admixes dispersed saccharin into said toothpowder.

10. The method of claim 7 wherein said admixing admixes citric acid into said toothpowder.

11. The method of claim 7 wherein said admixing admixes flavor oil into said toothpowder.

12. The method of claim 7 wherein said calcium carbonate abrasive particulate comprises individual calcium carbonate particles having independent calcium carbonate particle sizes, said fluoride ion source comprises particulate sodium monofluorophosphate and said method further comprises pulverizing, prior to said admixing, raw granulated sodium monofluorophosphate into said particulate sodium monofluorophosphate such that independent fluoride ion source particulate particle sizes of said particulated sodium monofluorophosphate are differentiated from said independent calcium carbonate particle sizes by not greater than 20 microns for at least 99 percent of said calcium carbonate particles.

13. The method of claim 7 wherein said admixing is performed by use of a ribbon blender.

14. The method of claim 13 wherein said ribbon blender has a first end and a second end and said admixing is performed by charging said blender with said calcium carbonate particulate and continuously adding a first pulverized stream of said particulate sodium monofluorophosphate to said first end of said ribbon blender and a second pulverized stream of said particulate sodium monofluorophosphate to said second end of said ribbon blender until said particulate sodium monofluorophosphate is admixed into said calcium carbonate particulate.

15. Toothpowder made by a process according to the method of claim 7.

\* \* \* \* \*